(12) United States Patent
Iyer

(10) Patent No.: US 7,700,793 B2
(45) Date of Patent: Apr. 20, 2010

(54) SYSTEMS AND METHODS FOR ESTERIFICATION AND TRANSESTERIFICATION OF FATS AND OILS

(75) Inventor: Satish Ramnathan Iyer, Calgary (CA)

(73) Assignee: Biosphere Environmental Energy LLC, Studio City, CA (US)

( * ) Notice: Subject to any disclaimer, the term of this patent is extended or adjusted under 35 U.S.C. 154(b) by 810 days.

(21) Appl. No.: 11/450,781

(22) Filed: Jun. 9, 2006

(65) Prior Publication Data
US 2006/0293533 A1  Dec. 28, 2006

Related U.S. Application Data

(60) Provisional application No. 60/727,893, filed on Oct. 18, 2005, provisional application No. 60/688,818, filed on Jun. 9, 2005.

(51) Int. Cl.
C07C 51/43 (2006.01)
(52) U.S. Cl. ...................................................... 554/174
(58) Field of Classification Search .................. 554/174
See application file for complete search history.

(56) References Cited

U.S. PATENT DOCUMENTS

| 4,032,550 A | 6/1977 | White et al. |
| 4,698,186 A | 10/1987 | Jeromin et al. |
| 5,532,392 A | 7/1996 | Gheorghiu |
| 6,712,867 B1 * | 3/2004 | Boocock ...................... 44/389 |
| 6,878,837 B2 | 4/2005 | Bournay et al. |

FOREIGN PATENT DOCUMENTS

| WO | WO 01/12581 A1 * | 2/2001 |
| WO | WO 03/040081 A1 * | 5/2003 |
| WO | WO 2004/048311 A1 | 6/2004 |

OTHER PUBLICATIONS

Suppes et al., "Transesterification of soybean oil with zeolite and metal catalysts", Elsevier B.V., pp. 1-14, Apr. 9, 2003.
International Search Report—PCT/US2006/022665.

* cited by examiner

*Primary Examiner*—Deborah D Carr
(74) *Attorney, Agent, or Firm*—Knobbe, Martens, Olson & Bear LLP

(57) ABSTRACT

Esterification and transesterification of fats and oils is conducted using one or more heterogeneous solid catalysts in the presence of an alcohol and a cosolvent. In one example, esterification of free fatty acids in fats and oils feedstock is conducted by contacting the feedstock with a solid catalyst having acidic groups. Transesterification of triglycerides in the feedstock is conducted by contacting the feedstock with a solid catalyst having basic groups. Single train continuous plant designs are described for near complete conversion of fats and oils by sequentially contacting the feedstock with heterogeneous acidic solid catalyst and basic solid catalyst.

43 Claims, 2 Drawing Sheets

SYSTEMS AND METHODS FOR ESTERIFICATION AND TRANSESTERIFICATION OF FATS AND OILS

CROSS-REFERENCE TO RELATED APPLICATIONS

This application claims the benefit of U.S. Provisional Application Nos. 60/688,818, filed Jun. 9, 2005, and 60/727,893, filed Oct. 18, 2005, both of which are incorporated herein by reference in their entirety.

BACKGROUND OF THE INVENTION

1. Field of the Invention

The invention relates to methods and systems for esterification and transesterification of fats and oils.

2. Description of the Related Art

Fats and oils consist mainly of triglycerides and free fatty acids in various proportions. Subjecting these fats and oils to esterification and/or transesterification reactions yield a mixture of esters and glycerol as the primary reaction products. The esters produced can be used as a biodiesel fuel or as components in other useful industrial and consumer products.

Many procedures currently used to convert fats and oils to esters involve mixing the fats or oils with an alcohol (such as methanol), miscible catalysts, and sometimes a co-solvent. The use of a co-solvent promotes the formation of single phase, preventing the separation of the alcohol and the fats or oils. Typically, an acidic miscible homogenous catalyst such as sulphuric acid dissolved in the alcohol is used to esterify free fatty acids, while a basic miscible homogenous catalyst such as sodium hydroxide or potassium hydroxide is used the transesterify the triglycerides. These catalysts are typically applied sequentially in a two-stage process. Heterogeneous catalysts have also been used for esterification and transesterification reactions using an oil/fat and an alcohol, but the oil and alcohol phase separation that occurs significantly impedes the reaction rate, thus resulting in long residence times lasting up to several hours and poor product yield.

SUMMARY

Use of such homogeneous catalysts present certain difficulties. For example, the alcohol and co-solvent remaining in the reaction products are typically removed by distillation; however, the catalysts are not as volatile and therefore remain as contaminants in the final product after distillation. Depending on the desired purity of the final product, expensive and time consuming additional processing may be required to remove the catalyst contaminants. In addition, commercial plants making use of homogeneous catalysts must operate in batch mode in order to repeatedly produce catalyst stock solutions. Such operation involves extensive labor, repeated exposure of workers to corrosive chemicals, and excessive wastage. Batch operations depend heavily on the skill of the operators, often resulting in inconsistent plant operation and product quality. Furthermore, utilization of corrosive acids require expensive metallurgy for constructing reactors, tanks, pipes, valves, pumps and other processing equipment that can withstand the corrosive environments. Accordingly, there is a need for improved processes and systems for the esterification and transesterification of fats and oils.

One embodiment disclosed herein includes a method of producing an ester from an oil or fat feedstock, the method including mixing the feedstock with an alcohol and a co-solvent, contacting the feedstock, alcohol and co-solvent mixture with a first solid heterogeneous catalyst comprising acidic groups to produce a first reaction mixture, and contacting the first reaction mixture with a second solid heterogeneous catalyst comprising basic groups to produce a second reaction mixture.

Another embodiment disclosed herein includes an ester production system having a first reaction vessel comprising a first solid catalyst that comprises acidic groups, the first solid catalyst adapted to catalyze conversion of free fatty acids to esters; a second reaction vessel comprising a second solid catalyst that comprises basic groups, the second solid catalyst adapted to catalyze conversion of tricglycerides to esters, the second reaction vessel in fluid communication with the first reaction vessel; and a pump configured to drive a mixture of an oil or fat feedstock and an alcohol sequentially and continuously through the first reaction vessel and the second reaction vessel.

Another embodiment disclosed herein includes a method of converting a triglyceride to one or more other esters, including mixing the triglyceride with an alcohol and co-solvent and contacting the triglyceride, alcohol and co-solvent mixture with a basic group anion exchange resin.

Another embodiment disclosed herein includes a method of converting free fatty acids to one or more other esters. The method includes mixing the free fatty acids with an alcohol and a co-solvent, and contacting the mixture with an acidic group cation exchange resin.

DETAILED DESCRIPTION OF CERTAIN EMBODIMENTS

In one embodiment, solid heterogeneous catalysts are used to effect the esterification of free fatty acids or the transesterification of triglycerides to produce esters from fats or oils. Use of such solid catalysts instead of homogenous catalysts facilitates separation of the catalysts from reaction mixtures. For example, solid catalysts can be removed by simple filtration or retained in a flow-through reaction vessel. Furthermore, plants utilizing solid catalysts can be operated in continuous mode instead of batch mode. In one embodiment, a solid heterogeneous catalyst having acidic groups is used to promote the esterification of free fatty acids in the presence of an alcohol and a co-solvent. For example, a solid catalyst may be used that has acidic surface groups or that is adapted to provide a hydrogen ion that catalyzes the esterification reaction. In one embodiment, a solid heterogeneous catalyst having basic groups is used to promote the transesterification of triglycerides in the presence of an alcohol. For example, a solid catalyst may be used that has basic surface groups or that is adapted to provide a hydroxide ion that catalyzes the transesterification reaction. More generally, in some embodiments, the acidic solid catalyst presents Lewis acidic groups on its surface or is adapted to yield a Lewis acid to the reaction mixture and the basic solid catalysts presents Lewis basic groups on its surface or is adapted to yield a Lewis base to the reaction mixture. In such embodiments, the co-solvent added to the reaction mixture promotes the formation of a single phase between the fat and the alcohol which greatly reduces the mass transfer resistances and speeds up the reaction.

The feedstock sources of free fatty acids and triglycerides may come from any suitable animal, plant, or algae derived fats or oils. Non-limiting examples of sources for such fats and oils include rapeseed oil, palm oil, sunflower seed oil, soya oil, coprah oil, cottonseed oil, castor oil, Jatropha seed oil, Pongamia seed oil, Yellow Grease, Used Frying Oil, tallow, and animal fat.

Figure 1:
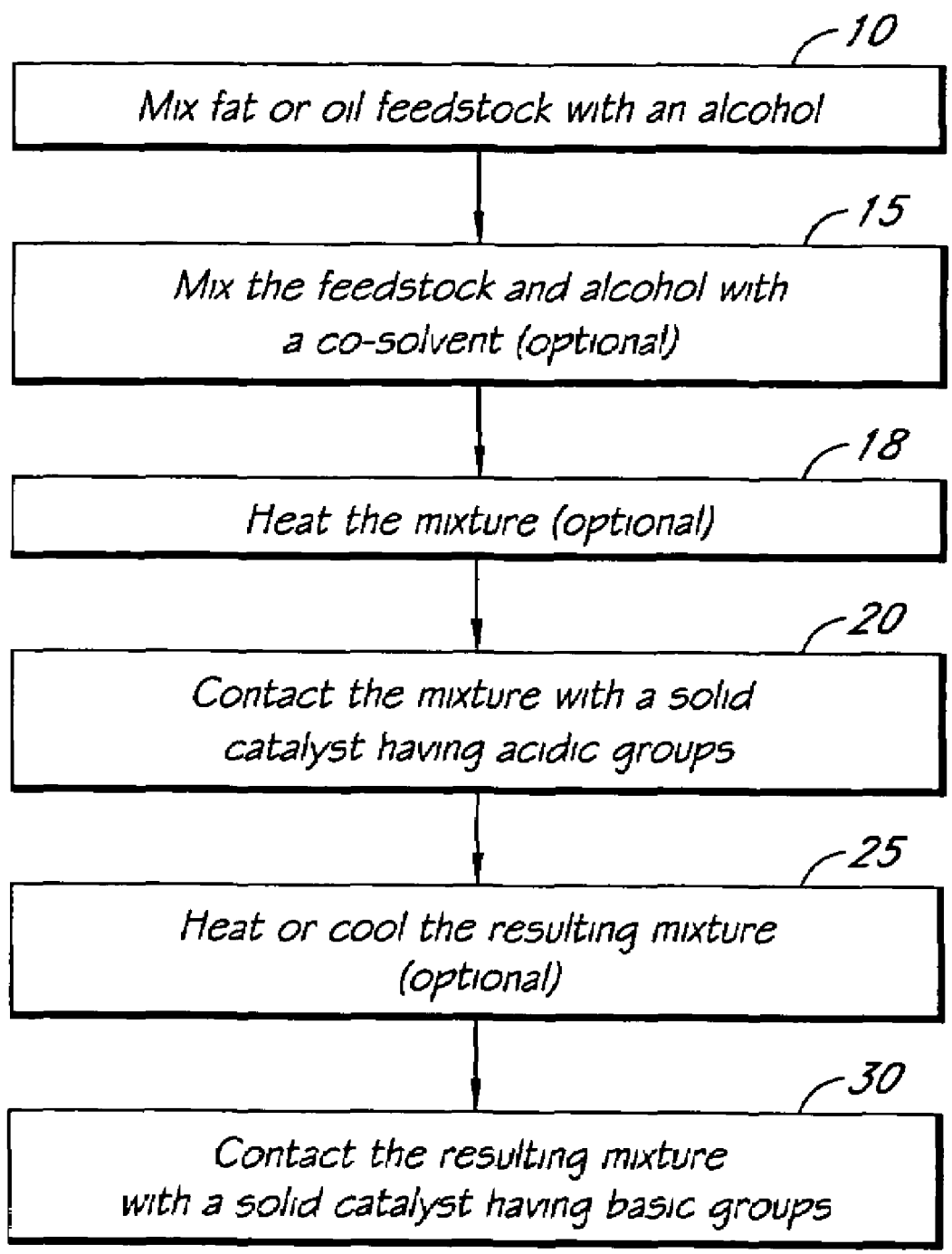
FIG. 1 is a flowchart illustrating an example process for esterification and transesterification of fats and oils.

One example method for converting fats or oils feedstock into esters is illustrated by the flowchart in FIG. 1. At block 10 the feedstock is first mixed with an alcohol. At block 15, a co-solvent is optionally added to the feedstock/alcohol mixture to promote the formation of a single phase. Use of a co-solvent advantageously reduces the likelihood that the alcohol will separate from the fats and oils, which would complicate processing and slow the reaction down. Any co-solvent suitable for promoting the formation of a single phase mixture may be used. Non-limiting examples include tetrahydrofuran (THF), 1,4-dioxane, diethylether, methyltertiarybutylether (MTBE), and diisopropylether. Next at block 18, the feedstock mixture is optionally heated to a desired first-stage reaction temperature. At block 20, the feedstock mixture is contacted with a solid catalyst comprising acidic groups. In the presence of the catalysts disclosed herein, the alcohol reacts with the free fatty acids and triglycerides in the feedstock to produce esters. In some embodiments, the alcohol is an alkanol such as a mono-alkanol and the ester product is an alkyl ester. In some embodiments, the alkanol is a $C_{1-4}$-monoalkanol (e.g., methanol or ethanol). At block 25, the mixture resulting from the reaction occurring at block 20 is optionally heated or cooled to a desired second-stage reaction temperature. Finally at block 30, the mixture is contacted with a second solid catalyst comprising basic groups.

Depending on the particular embodiment, steps may be added to those depicted in the flowchart of FIG. 1 or some steps may be removed. For example, in a modified embodiment excess alcohol and co-solvent are separated from the reaction mixture by distillation or another equivalent technique, esters are separated form the by product glycerol using a centrifuge, gravity settling or another equivalent technique, and the ester phase is water washed to obtain high purity esters. Optionally, the ester and glycerol are dried separately to obtain even higher purity levels. In addition, the order of steps may be rearranged depending on the application.

In one embodiment, the ester products are used as a biodiesel fuel for operating diesel engines. Other non-limiting uses of esters include jet fuel for aircraft; fuel for powering turbines, compressors, pumps, and electricity generators; lubricating oils including non-toxic and bio-degradable lubricants such as for use in drilling operations involving land and water based drilling rigs; fuel additives; grease; perfumes; pharmaceuticals; printing ink; food additives; cosmetics; and healthcare products.

In certain embodiments where fats or oils feedstock is used that substantially lack free fatty acid, only the solid catalyst having basic groups is used. Conversely, feedstock comprising substantially only free fatty acids can be converted using only the acidic group containing catalyst. In some embodiments, two or more solid catalysts may be used in succession. For example, in feedstock comprising a mixture of free fatty acids and triglycerides, the feedstock may first be contacted with a solid catalyst having acidic groups to convert the free fatty acids to alkyl esters. After reaction in the presence of the first catalyst, the reaction products may then be contacted with a solid catalyst having basic groups to convert the triglycerides to alkyl esters and glycerol.

In one embodiment, the solid catalysts for use as described herein are substantially immiscible and substantially insoluble in methanol, fats, oils, and/or co-solvents such as tetrahydrofuran (THF). In some embodiments, the solid catalyst includes a substantially non-reactive support for immobilized reactive groups such as acidic or basic groups. Non-limiting examples of suitable solid catalysts include ion exchange resins, supported lipase or other suitable catalytic enzymes, supported or unsupported metals or metal oxides, and other immobilized acidic or basic groups. In one embodiment, the acidic group containing solid catalyst is a cation exchange resin. Such a resin can be used provide hydrogen ions to a reaction mixture. Similarly, in one embodiment, the basic group containing catalyst is an anion exchange resin, which can be used to provide hydroxide ions to a reaction mixture. Suitable substrates for supporting immobilized catalytic groups include zeolites or other silica or alumina based supports, graphitic materials such as activated carbon, rocks or stones, wood or other organic material from vegetation or animals, and synthetic fibers or plastics. The catalyst solids can be any suitable shape including spherical, cylindrical, cubical, ring-shaped, oval, fibrous, woven, compacted sheets, and irregular shapes. In some embodiments, the solids take the form of a powder, granular, coarsely ground, or finely ground substance. In some embodiments, the active surface area of the solid catalyst is enhanced by using highly porous substrates or woven fiber substrates. Increased surface area may allow for reduced reaction temperature and pressure and reduced equipment sizes.

Typically, esterfication and transesterification reactions are performed at atmospheric pressures. At these pressures, reaction temperatures are typically from about 40° C. to about 65° C. to ensure that the reaction mixture does not boil. A faster reaction rate can be obtained by increasing the reaction temperature. These higher temperatures can be achieved by performing the reaction at higher pressures. Accordingly, in one embodiment, the reaction processes described herein are carried out at pressures from about 50 kPa gauge to about 5000 kPa gauge. In another embodiment, the reaction processes described herein are carried out at pressures from about 1000 kPa gauge to about 5000 kPa gauge. At these pressures, reaction temperatures between from 50° C. to about 300° C. may be used, resulting in faster conversion rates. Suitable reaction pressures and temperatures may be chosen based on the boiling point of the components in the reaction mixture and the ratio of solvents and reactants in the mixture. Pressure and temperature can be as high as the fats, oils, other liquids involved and the catalyst can stably exist without undergoing degradation. Much higher rates of reaction can be achieved by performing the reaction at higher temperatures and pressures. Higher reaction rates reduce the required residence time in the reactor resulting in much smaller reactor size. In one embodiment, residence time in a given reactor is less than one hour (e.g., about 10 to about 30 minutes).

Some embodiments include systems for conducting the reactions and processes described herein. For example, a production plant may be used having one or more reactors configured to provide a continuous processing system. In some embodiments, the continuous processing system has a single train configuration with two or more reactors in series. In one such embodiment, a reaction mixture consisting of oil or fat, alcohol (e.g., methanol or ethanol), and a co-solvent is fed to a first reactor filled with the solid heterogeneous acidic surface catalyst for esterification of the free fatty acids. The reaction mixture discharge from the first reactor is then fed to a second reactor filled with a basic surface solid heterogeneous catalyst for the second stage transesterification of triglycerides. The discharge from the second stage reactor can be flashed or distilled under atmospheric pressure or vacuum to recover excess alcohol and the cosolvent, leaving behind the product mix of alkyl esters and glycerol. In some embodiments, the product mix is water washed to enhance the phase separation between the esters and glycerol layers. Water washing also helps in extracting out the dissolved glycerol in the ester. The esters can be separated from glycerol by gravity settling in large tanks or by means of using centrifuges or other separation equipment to yield pure uncontaminated ester and clean glycerol separately. Fine filters can be incorporated appropriately to reduce the likelihood of contaminating the feedstock, other processed material, or the solid catalyst with floating solids, thereby improving ester quality.

The reactors can be designed as a packed bed with the liquid reactant mixture continuously flowing through the solid catalyst bed accomplishing intimate contact with the catalyst to achieve high conversion. In other embodiments, the reactor type can be a fluidized bed, moving bed, circulating bed, elutriated bed, agitated bed, boiling bed, or another suitable design for contacting solid catalysts with a liquid medium. In moving bed, circulating bed, or elutriated bed configurations, the solid catalyst may be continuously separated in a cyclone arrangement and fed back into the reactor. The choice of the reactor type may depend on the type of solid catalyst and properties of the reaction mixture. In an example embodiment, the reactor is operated at a pressure and temperature that depend on ambient conditions and the desired conversion.

In some embodiments where a two-stage process-is utilized (such as an esterification stage followed by a transesterification stage), each stage can utilize more than one reactor. For example, two or more reactors may be used in each reaction stage to enhance the level of completion of the esterification and transesterification reactions. The set of reactors in each stage may be connected by series or parallel pipe connection to achieve the desired level of conversion to product. In some embodiments, the process fluid discharge from an upstream reactor is processed to separate and remove moisture, glycerol and other less desirable by-products formed in the upstream reactor before being fed to a downstream reactor (e.g., by water washing). Eliminating the less desirable by-products of the reaction in the intermediate steps helps the reaction progress faster to completion, thereby achieving higher ester conversion in shorter residence time.

In some embodiments, a recycle system may be included where the reaction products are continuously fed back to the inlet of the reactor using a pump or an ejector device one or more times to increase product yield and purity.

Figure 2:
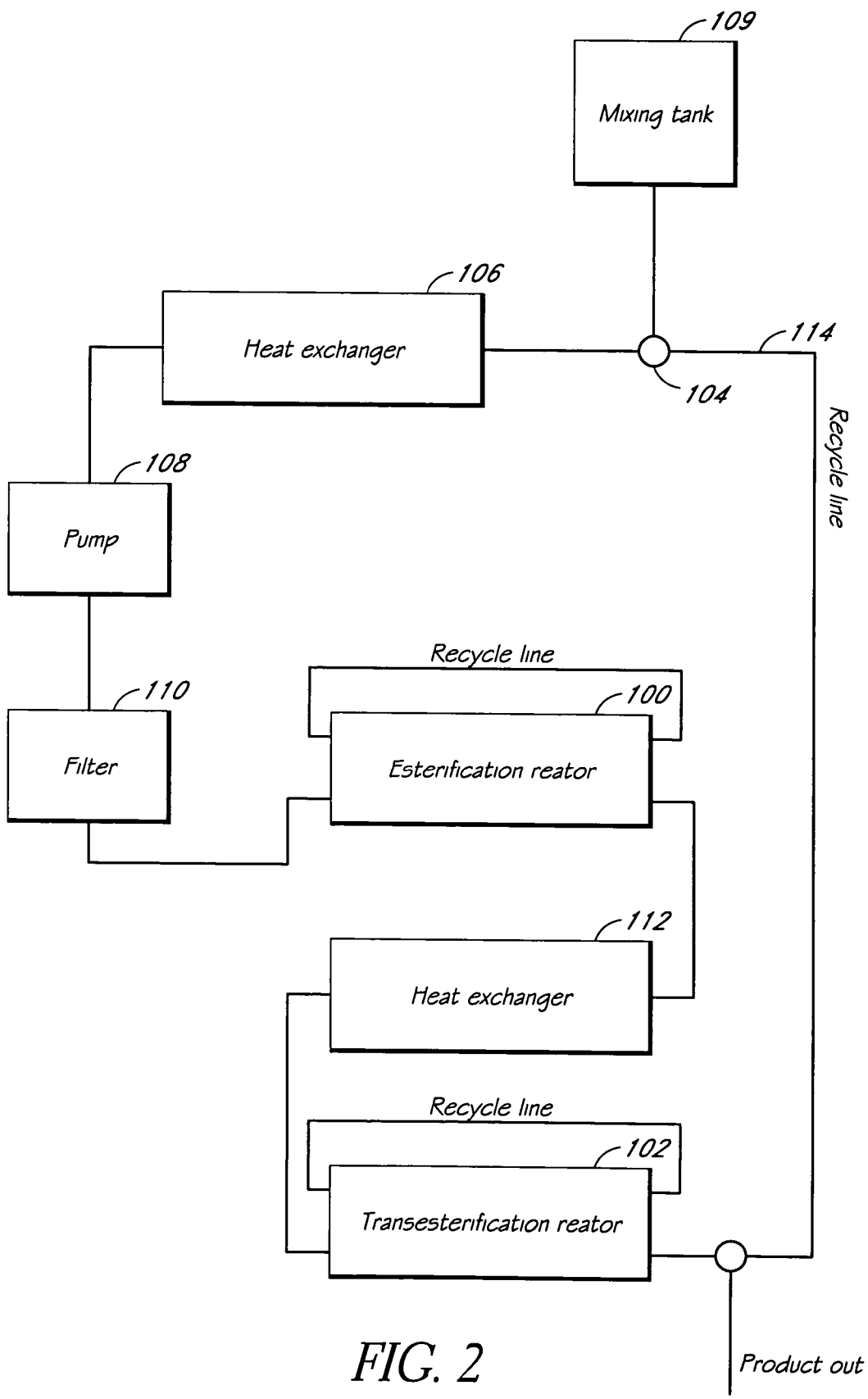
FIG. 2 is a schematic illustrating an example plant design suitable for the esterification and transesterification of fats and oils.

FIG. 2 is a schematic illustrating one exemplary plant design suitable for use as described herein. This design includes two packed column reactors 100 and 102. The reactors 100 and 102 are packed with solid catalysts as described herein. The catalysts may be in the form of spheres. In one embodiment, the spheres have diameters ranging from about 0.3 mm to about 1 mm. Other shapes such as cylindrical, pyramidical, cubical, or irregular random shapes such as long needles, short or long fibers, slabs, mesh, crushed powder etc. can also be used to pack the columns. The catalyst can also be formed in shapes like rashig rings, pall rings, berl saddles or other shape packing. The catalyst can also be in the form of structured packing.

The first column reactor 100 contains a solid catalyst having acidic groups. The catalyst can be packed tightly to form a conventional packed bed. Mesh plates at either end of the reactor can be used to keep the solids in packed condition while allowing the liquid to percolate through the bed. Other forms of packing are optionally incorporated to keep the bed in packed condition. The second column reactor 102 may be identical in structure to the first reactor 100, but is packed with solid catalyst having basic groups. Each reactor may be insulated or equipped with a jacket around their entire length. A heating/cooling medium such as steam or water may be flowed though the jackets to control the temperature of each reactor. The reactors may be mounted vertically, inclined, or horizontally. The reactor inlet and outlet can be at the same elevation or vertically separated.

The reactant mixture (e.g., fat or oil feedstock mixed with an alcohol and co-solvent) is drawn into the system via pump 104, passing first through a heat exchanger 106. The heat exchanger 106 may be used to heat the reactant mixture to the temperature desired for reaction in the first column reactor 100. One or more additional pumps 108 may be included at suitable points in the single train system (e.g., downstream of the heat exchanger 106) to provide for fluid flow and pressurization throughout the system. In other embodiments, the one or more additional pumps 108 are located at positions within the reaction system other than depicted in FIG. 2.

An external jacketed mixing tank 109 may be attached to the pump 104, such that the pump suction may draw reactant mixture from the mixing tank into the reactor system. In one embodiment, the mixing tank 109 is equipped with an air operated agitator. Other types of mixing tanks and other mixing methods may also be used (e.g., using an agitator driven by an electric motor or a static mixer). The feedstock, alcohol, and co-solvent are mixed in the external tank 109 prior to being sucked into the reactor system by pump 104. In one embodiment, the pump 104 and the reactors 100 and 102 operate between about 50psi and 600 psi gauge, however, other pressures may be employed as desired.

Fats and oils may be preconditioned prior to introduction into the mixing tank 109. In some embodiments, the pretreatment operations are performed before storing the feedstock in bulk. Alternatively the feedstock can be stored without much processing and the conditioning pre-treatment can be applied while extracting the feedstock from bulk storage before pumping it to other downstream process units (e.g., mixing tank 109). In some embodiments, preconditioning includes melting fats so that they can more easily be processed. Feedstock can also be cleaned using equipment to separate non-saponifiable matter. In certain applications, starting with a cleaner feedstock yields better quality product, thereby reducing or eliminating the need for product refining equipment. The pre-treatment operations may include settling, decanting, and filtering to eliminate free water and suspended solids. It can also include subsequent drying in order to separate and remove emulsified or bound moisture and other volatile compounds. The drying operation can be performed in vacuum evaporators or by means of employing a solid drying media in the form of packed bed or fluidized or moving bed. Any suitable liquid drying media can also be used by employing suitable contacting and separating equipment. In some embodiments, a total moisture content of less than about 500 ppm is obtained prior to mixing the feedstock with the alcohol and co-solvent. Low moisture content in the feedstock promotes higher final product purity. In some embodiments, oils in the feedstock are de-gummed, bleached and refined prior to introduction into the mixing tank 109. In certain embodiments, oils and fats are treated to adsorb and separate dissolved organic matter such as proteins, sterols, hormones and the like. In other embodiments, before admitting the feedstock into the main reactor, the oils and fats are treated to adsorb or exchange and separate dissolved inorganic salts and free radicals using, for example, a cation and anion exchange medium.

In some embodiments, the feedstock pre-treatment process also involves employing membranes for filtering and eliminating miscible homogenous contaminants. Membranes can be used for separating cholesterol, sterols, steroids, hormones, proteins and other non-saponifiable matter present in the animal and vegetable fats and oils. Lowering the contaminant concentration in the feedstock promotes achieving higher yields and purer products.

As depicted in FIG. 2, filter 110 may be included to remove any remaining particulate matter in the reactant mixture prior to introduction of the mixture into the first column reactor 100. A second heat exchanger 112 may be included upstream of the second column reactor 102 so that the temperature of fluid flowing into the second reactor 102 may be controlled independently from the fluid temperature in the first reactor 100. The heat exchangers 106 and 112 may be designed such that the process fluid flows in an inner pipe while heating/cooling medium (e.g., water or steam) flows through an outer pipe/shell or vice versa. Other types of heat exchangers (for example, Plate heat exchangers, Spiral heat exchangers) can be employed as desired.

The heat exchangers 106 and 112, reactors 100 and 102, pump 108, and filter 110 may be interconnected in a single train by suitable pipes or tubing with appropriate valves for isolation and for flow control. Alternative configurations of the system components may also be used. Pressure and temperature gauges may be provided at appropriate locations. Other instruments useful for controlling the process for continuous operations may be provided as appropriate.

An optional recycle line 114 may be included to return product from the second reactor 102 to the first heat exchanger 106 if it is desirable to use multiple passes to increase yield and purity. In some cases the output from a reactor can be recycled back to the input of the same reactor to improve quality of yield. After the final reaction products exit the reaction system, refining equipment may be used to separate solid and liquid contaminants. Solids and liquids can be separated using suitable filters, cyclones, hydroclones or centrifuges. Miscible liquid contaminants can be separated using absorption or adsorption using solid beds or by employing liquid-liquid extraction techniques or by water washing. Immiscible liquids, such as the alkyl ester and glycerol products, can be separated using gravity settling tanks or centrifuges. Refining may also include using drying techniques, with or without using vacuum. In all cases, the refining equipment can optionally be configured in a single train fashion such that the entire process operates in continuous mode. In one embodiment, mixtures of methylester and glycerol produced in the process can be stored in large tanks to allow for gravity separation or can be processed using centrifuges to obtain methyesters and glycerol separately.

EXAMPLES

Example 1

—Laboratory Conversion using Ion Exchange Resins

Animal fat (Yellow Grease) obtained from Lakeside Packers, Brooks AB, a beef packaging unit, was used as the raw fat feedstock. The animal fat contained less than 1 % moisture and about 1 % free fatty acid. In order to simulate higher free fatty acid content in the fat, 99% pure oleic acid was added to the animal fat to obtain a free fatty acid fat concentration of 15% w/w. A standard laboratory cylindrical high pressure autoclave (2 L volume) was used for the reaction vessels. The autoclave had provisions for mixing, electrical heating, water cooling and pressurizing the contents. The autoclave was pressurized using a high pressure nitrogen bottle.

100 gm of animal fat containing 15% w/w free fatty acids was placed in a 2 L round bottom flask. Methanol in the ratio of 60:1 and 336 grams of THF were added and completely mixed to a single phase. The methanol and THF used were of more than 99% purity. The entire contents of the round bottomed flask were transferred into the autoclave and 375 grams of a strong acidic cation exchange resin (C381BH from US FILTER®) was added. The autoclave was pressurized to 2068 kPa gauge (300 psi gauge) and heated to 120° C. for 1 hour during which time the mixer was operated at 600 rpm. The autoclave contents were then emptied into a vacuum filter to filter out the cation resin catalyst. The filtrate was transferred into a clean autoclave for the second stage reaction and 375 grams of a strong basic anion exchange resin (A674BOH from US FILTERS®) was added. This mixture was pressurized to 2068 kPa gauge (300 psi gauge) and heated to 60° C. for 1 hour during which time the mixer was operated at 600 rpm. After an hour, the entire contents of the autoclave were transferred into a vacuum filter to separate the anion resin catalyst. The filtrate was then transferred into a round bottom flask and mounted on a vacuum roto-vap separator to distill out the excess methanol and THF. After about 10 minutes, separate glycerol and ester layers appeared in the round bottom flask. The contents were then centrifuged and the top ester layer was decanted from the glycerol, which remained as the bottom layer. Without any further treatment, a sample of the methylester was analyzed on a Hewlett-Packard Gas Chromatograph analyzer. The results indicated that more than 99.9% conversion was obtained. The conversion reaction at least partially depends on the molal ratio of methanol to fat. For example, in one embodiment the molal ratio of methanol to fat is between about 10:1 and about 60:1, which results in a conversion ratio between about 85% and about 99.9%.

The experiments were repeated with pressures ranging from 689 kPa gauge (100 psi gauge) to 2068 kPa gauge (300 psi gauge), temperatures from 50 ° C. to 120° C., methanol molar ratios ranging from 40:1 to 60:1, and residence times ranging from 30 minutes to 60 minutes. The ester conversions achieved ranged from about 90% to about 100%. Higher pressures, higher temperature, higher methanol ratios, and higher residence times generally resulted in an increased rate of reaction. Experiments were also performed using recycled vegetable oil from a restaurant and oil from soya, corn, sunflower, and canola seeds with similar results. Experiments were also conducted using ethanol instead of methanol, achieving over 95% conversion.

Example 2

—Pilot Plant

A single train continuous operation plant was constructed using two packed column reactors. The first reactor was packed with 10 liters of a strong acidic cation exchange resin (C381BH from US FILTERS®) in the form of about 0.3 mm diameter spheres. The second reactor was packed with 10 liters of a strong basic anion exchange resin (A674BOH from US FILTER®), also in the form of 0.3 mm to 1 mm diameter spheres. Both columns measured four inches (4") in diameter and five feet (5') in length and were equipped with a six inch (6") diameter jacket around their entire length to provide temperature control. Heat exchangers were provided upstream of both reactors. The reactor columns and heat exchangers were connected in series forming a single train, interconnected by ½" tubes with appropriate ball valves for isolation and needle valves for flow control. All columns were mounted vertically with the whole unit sitting on a seven foot by three foot base frame and measuring about eight feet (8') in height. A compressed air operated reciprocating piston pump was used to feed the unit.

Animal fat was pre-conditioned by melting, filtering, and vacuum drying. A jacketed mixing tank was warmed to about 50° C. and then the melted fat, methanol, and THF were added with mild agitation. The mix consisted of 6000 gms of animal fat with a methanol mole ratio ranging between 40 to 60 and a THF mole ratio between 10 to 15.

The first reactor column was pre-heated and maintained between 80° C. to 120° C. using steam. The second reactor column was pre-heated and maintained at 50° C. to 60° C. The reaction mixture was then pumped into the pilot unit by supplying compressed air to the pump. The pump flow capacity was controlled by controlling compressed air pressure supplied to the pump. The reaction mixture was first passed through a heat exchanger, which was heated by steam. The reaction mixture temperature reached 120° C. at the exit of the heat exchanger and overflowed into the first reactor catalyst bed. The reaction mixture flow rate was adjusted to achieve a flow of about 10 L/hr.

After exiting the first reactor column, the reaction mixture overflowed into a second heat exchanger where it was cooled to 60° C., using water as the cooling medium. The mixture subsequently entered into the second reactor column. The flow rate through the second reactor remained the same as in the first reactor, thereby forming a single train system without recycle.

A two stage needle valve system mounted on the discharge of the reactor was used to control the back pressure in the pilot unit and acted as the let down valve to drop the product fluid to atmospheric pressure. The pilot unit from pump discharge to the final let down valve was maintained at about 300 psi gauge. The reaction product was discharged into portable pails. The product mixture was then evaporated under vacuum to separate and recover methanol and THF, leaving behind a mixture of methyl esters and glycerol. This mixture was then filtered to eliminate solids precipitating from the fat and centrifuged to separate the methylester from glycerol. The top layer from the centrifuge was decanted to obtain almost pure alky ester suitable for use as biodiesel.

Although the invention has been described with reference to embodiments and examples, it should be understood that numerous and various modifications can be made without departing from the spirit of the invention.

What is claimed is:

1. A method of producing an ester from a fatty feedstock material, comprising:
    mixing the feedstock with an alcohol and a cosolvent;
    contacting the feedstock, alcohol, and cosolvent mixture with a first substantially insoluble solid catalyst comprising acidic groups to produce a first reaction mixture; and
    contacting the first reaction mixture with a substantially insoluble second solid catalyst comprising basic groups to produce a second reaction mixture.

2. The method of claim 1, wherein the fatty feedstock is a material selected from the group consisting of one or more oils, one or more fats, and combinations thereof.

3. The method of claim 1, further comprising removing at least a portion of one or more components of the first reaction mixture prior to contacting it with the second solid catalyst.

4. The method of claim 1, wherein the alcohol is a $C_{1-4}$ alkanol.

5. The method of claim 1, wherein the alcohol is methanol or ethanol.

6. The method of claim 1, wherein the first solid catalyst comprises a cation exchange resin.

7. The method of claim 1, wherein the second solid catalyst comprises an anion exchange resin.

8. The method of claim 1, wherein the mixing comprises using a cosolvent to produce a single phase mixture.

9. The method of claim 1, wherein the cosolvent is tetrahydrofuran.

10. The method of claim 1, wherein contacting the feedstock, alcohol, and cosolvent mixture with the first solid catalyst is conducted at a pressure between about 50 kPa gauge to about 5000 kPa gauge.

11. The method of claim 1, wherein contacting the feedstock, alcohol, and cosolvent mixture with the first solid catalyst is conducted at a pressure between about 1000 kPa gauge to about 5000 kPa gauge.

12. The method of claim 1, wherein contacting first reaction mixture with the second solid catalyst is conducted at a pressure between about 50 kPa gauge to about 5000 kPa gauge.

13. The method of claim 1, wherein contacting first reaction mixture with the second solid catalyst is conducted at a pressure between about 1000 kPa gauge to about 5000 kPa gauge.

14. The method of claim 1, wherein any given portion of the feedstock contacts the first solid catalyst for less than one hour.

15. The method of claim 1, wherein any given portion of the first reaction mixture contacts the second solid catalyst for less than one hour.

16. A method of converting a triglyceride to one or more other esters, comprising:
    mixing the triglyceride with an alcohol and a cosolvent; and
    contacting the triglyceride, alcohol, and cosolvent mixture with an anion exchange resin.

17. The method of claim 16, wherein the alcohol is a $C_{1-4}$ alkanol.

18. The method of claim 16, wherein the alcohol is methanol.

19. The method of claim 16, wherein the mixing comprises mixing a fat or oil feedstock with the alcohol and cosolvent.

20. The method of claim 16, wherein the mixing producing a single phase mixture.

21. The method of claim 16, wherein the cosolvent is tetrahydrofuran.

22. The method of claim 16, wherein contacting the triglyceride, alcohol, and cosolvent mixture with the anion exchange resin is conducted at a pressure between about 50 kPa gauge to about 5000 kPa gauge.

23. The method of claim 16, wherein contacting the triglyceride, alcohol, and cosolvent mixture with the anion exchange resin is conducted at a pressure between about 1000 kPa gauge to about 5000 kPa gauge.

24. The method of claim 16, wherein at least about 90% of the triglyceride is converted to the one or more other esters.

25. The method of claim 16, wherein at least about 95% of the triglyceride is converted to the one or more other esters.

26. The method of claim 16, wherein at least about 99% of the triglyceride is converted to the one or more other esters.

27. The method of claim 16, wherein any given portion of the triglyceride, alcohol, and cosolvent mixture contacts the anion exchange resin for less than one hour.

28. A method of converting a free fatty acid to one or more other esters, the method comprising:

mixing the free fatty acid with an alcohol and a cosolvent; and contacting the free fatty acid, alcohol, and cosolvent mixture with a cation exchange resin.

29. The method of claim 28, wherein the alcohol is a $C_{1-4}$ alkanol.

30. The method of claim 28, wherein the alcohol is methanol.

31. The method of claim 28, wherein the mixing comprises mixing a fat or oil feedstock with the alcohol and cosolvent.

32. The method of claim 28, wherein the mixing producing a single phase mixture.

33. The method of claim 28, wherein the cosolvent is tetrahydrofuran.

34. The method of claim 28, wherein contacting the free fatty acid, alcohol, and cosolvent mixture with the cation exchange resin is conducted at a pressure between about 50 kPa gauge to about 5000 kPa gauge.

35. The method of claim 28, wherein contacting the free fatty acid, alcohol, and cosolvent mixture with the cation exchange resin is conducted at a pressure between about 1000 kPa gauge to about 5000 kPa gauge.

36. The method of claim 28, wherein at least about 90% of the free fatty acid is converted to the one or more other esters.

37. The method of claim 28, wherein at least about 95% of the free fatty acid is converted to the one or more other esters.

38. The method of claim 28, wherein at least about 99% of the free fatty acid is converted to the one or more other esters.

39. The method of claim 28, wherein any given portion of the free fatty acid, alcohol, and cosolvent mixture contacts the cation exchange resin for less than one hour.

40. The method of claim 1, further comprising removing moisture from the first reaction mixture prior to contacting it with the second solid catalyst.

41. The method of claim 40, wherein removing moisture comprises using liquid drying media.

42. The method of claim 28, further comprising removing moisture from the mixture.

43. The method of claim 41, wherein removing moisture comprises using liquid drying media.

* * * * *